United States Patent [19]
Tura et al.

[11] Patent Number: 5,609,161
[45] Date of Patent: Mar. 11, 1997

[54] OROFACIAL MYOGRAPHIC MEASUREMENT METHOD

[76] Inventors: Ronald E. Tura, 1598 Hillgrade Ave., Alamo, Calif. 94507; Glen F. Bailey, 1920 Carquinez Ave., Richmond, Calif. 94805

[21] Appl. No.: 464,357

[22] Filed: Jun. 5, 1995

Related U.S. Application Data

[62] Division of Ser. No. 184,294, Jan. 21, 1994, Pat. No. 5,452,727.

[51] Int. Cl.$^6$ ............................................. A61B 5/103
[52] U.S. Cl. ............................................. 128/777
[58] Field of Search ............................. 128/774, 776, 128/777, 780, 782, 896, 860, 865

[56] References Cited

U.S. PATENT DOCUMENTS

| | | | |
|---|---|---|---|
| 3,661,148 | 5/1972 | Kolin | 128/774 X |
| 4,198,967 | 4/1980 | Dror | 128/860 |
| 4,304,227 | 12/1981 | Samelson | 128/860 X |
| 4,402,306 | 9/1983 | Okano et al. | 128/777 X |
| 4,402,327 | 9/1983 | Lambert et al. | 128/774 |
| 4,521,186 | 6/1985 | Wodlinger et al. | 128/777 X |
| 4,593,686 | 6/1986 | Lloyd et al. | 128/860 X |
| 4,676,240 | 6/1987 | Gardy | 128/860 X |
| 4,687,002 | 8/1987 | Lahr | 128/774 |
| 4,934,378 | 6/1990 | Perry, Jr. | 128/777 X |
| 4,949,729 | 8/1990 | Haski | 128/774 |
| 5,090,421 | 2/1992 | Wagoner III | 128/774 |
| 5,190,051 | 3/1993 | Wilson | 128/777 |
| 5,212,476 | 5/1993 | Maloney | 128/777 X |
| 5,218,970 | 6/1993 | Turnbull et al. | 128/774 X |

Primary Examiner—Sam Rimell
Attorney, Agent, or Firm—Elliot B. Aronson

[57] ABSTRACT

A myographic measurement method for direct strength measurement of the orofacial muscles, in particular, the lip and tongue muscles. A pressure-sensitive probe is placed in engagement with the orofacial muscle being tested. The probe provides a pressure response representative of the muscle strength under test. The probe is coupled to a transducer that converts the probe's pressure response in real time to an electrical signal representative of the force exerted on the probe by the muscle under test. The probe provides a representative pressure reading continuously over a test run of prescribed duration. The electrical signal generated in the test run is sampled and analyzed in real-time to determine a characteristic maximum pressure and hence characteristic maximum muscle strength achieved over the test run. The maximum muscle strength is provided in a form that may be incorporated directly into computerized patient records. The pressure-sensitive probe is provided by a balloon probe that is pneumatically coupled to a transducer. A strength measurement is made by holding the balloon probe against the muscle to be tested and having the patient press against the balloon probe with that muscle. To assist in holding the balloon probe in position a support fixture is provided that includes an anchor member that the patient retains in the mouth, typically gripped by the teeth, and a retaining member that is fixed to the anchor member and is shaped to retain the balloon probe in position against the lip muscle under test. Two illustrative shapes of support fixtures are illustrated for making measurements of the front upper and lower lip muscles and of lateral lip muscle thrust.

5 Claims, 6 Drawing Sheets

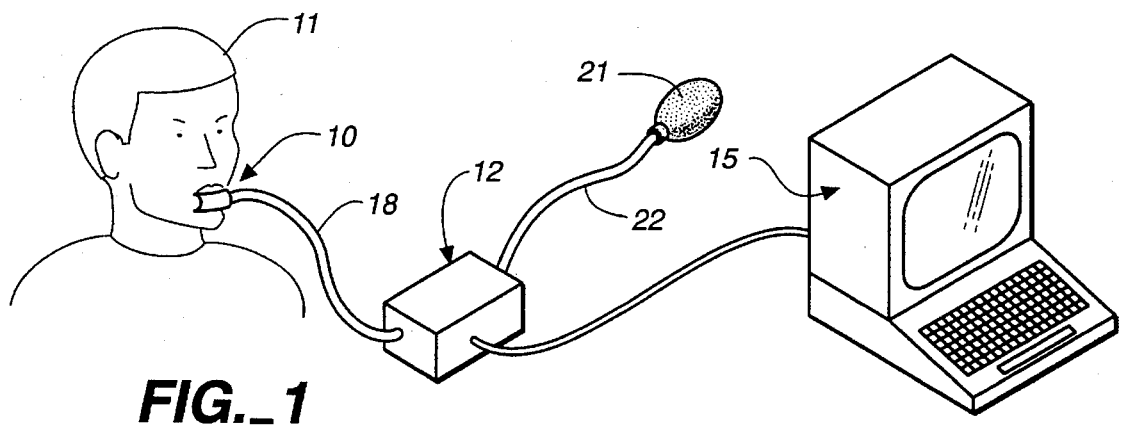
FIG._1
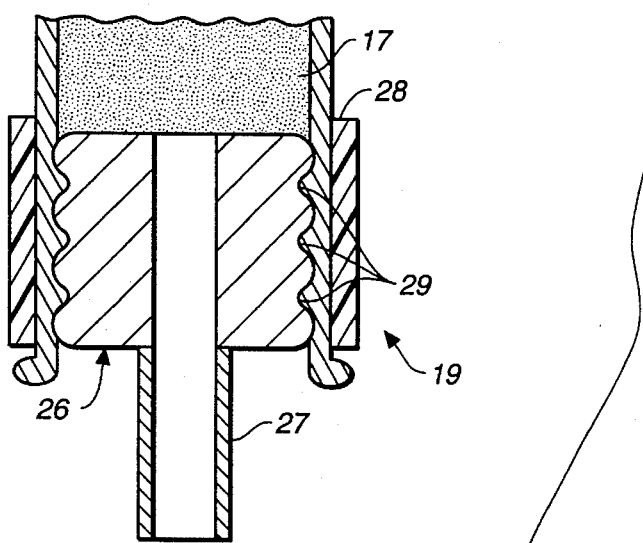
FIG._3
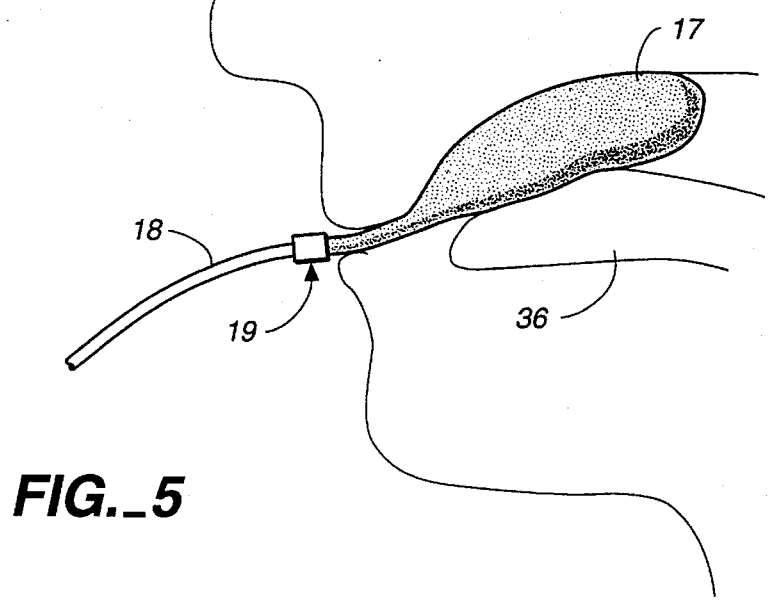
FIG._5

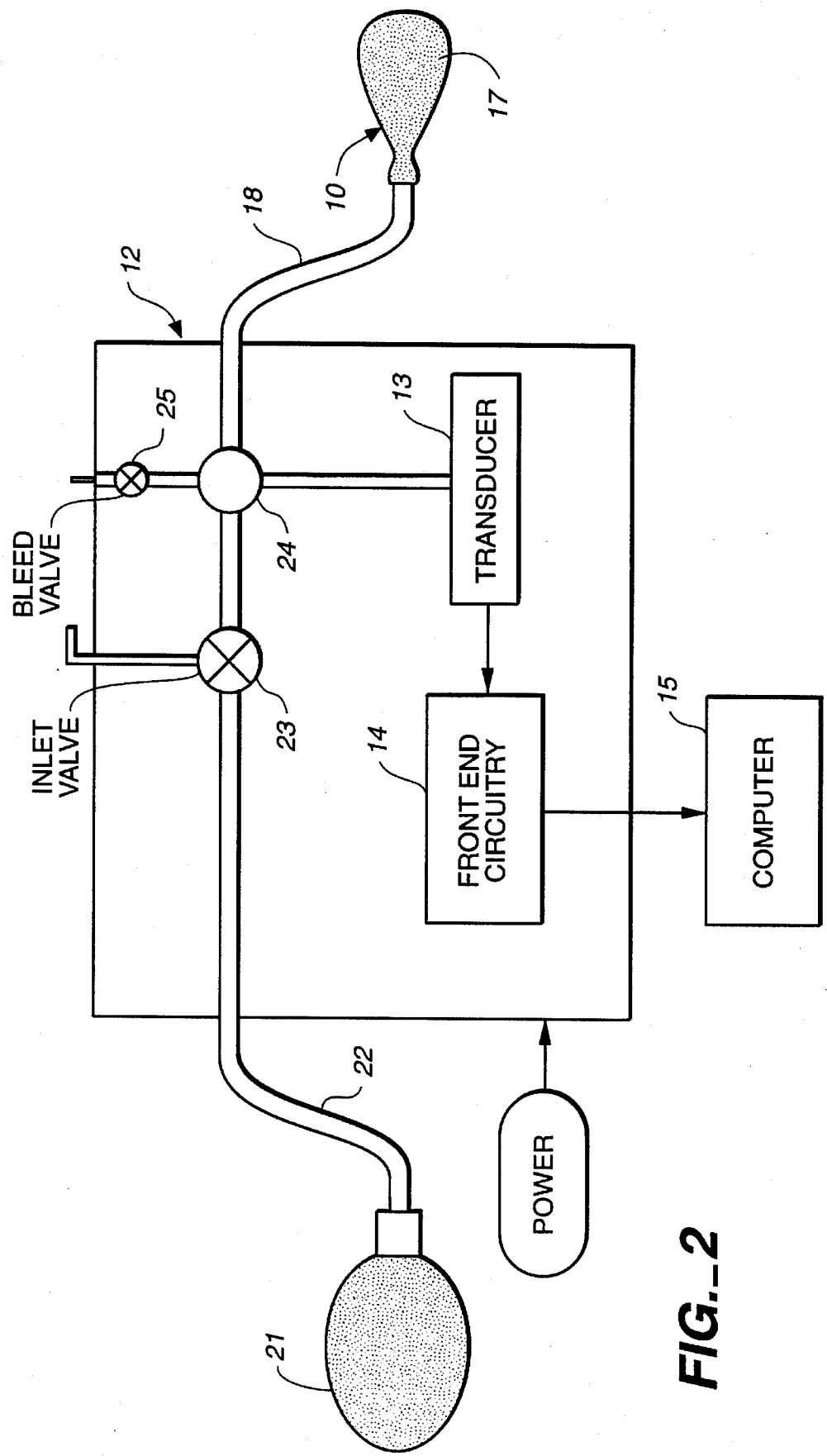
FIG._2

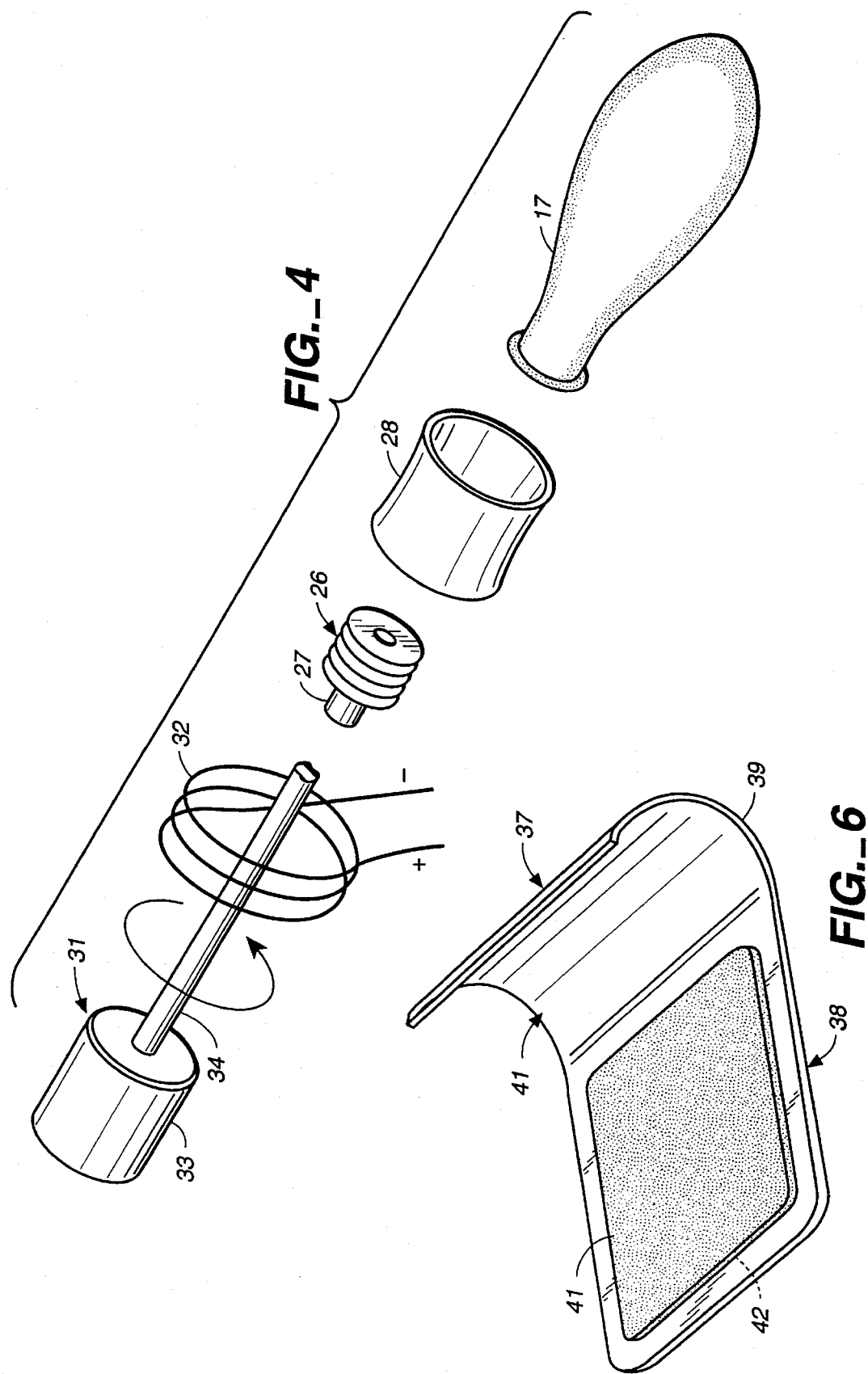

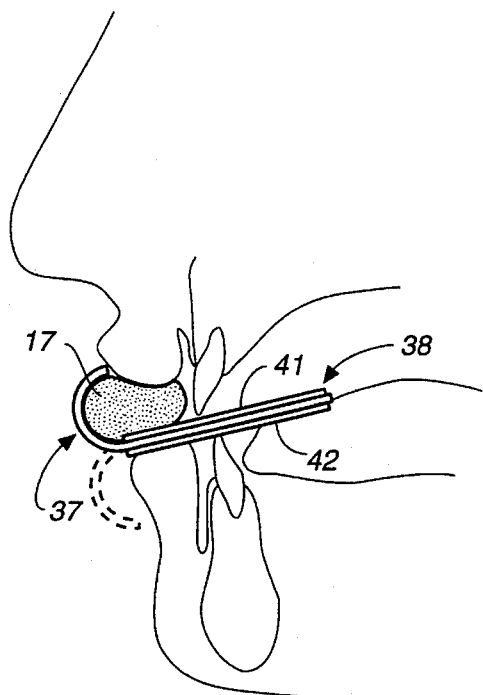
*FIG._7A*
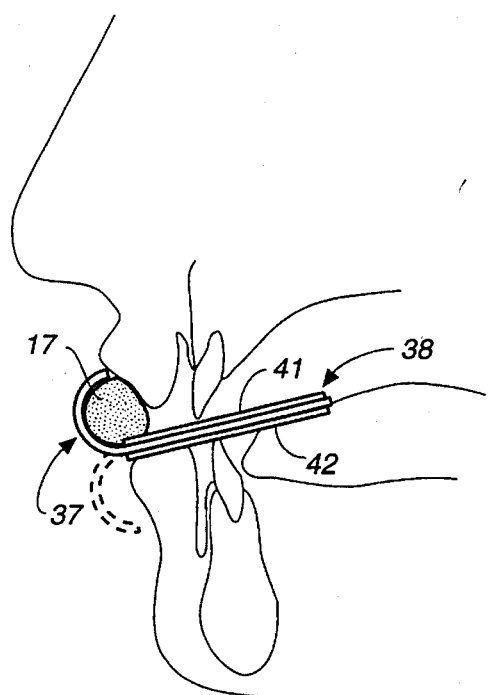
*FIG._7B*
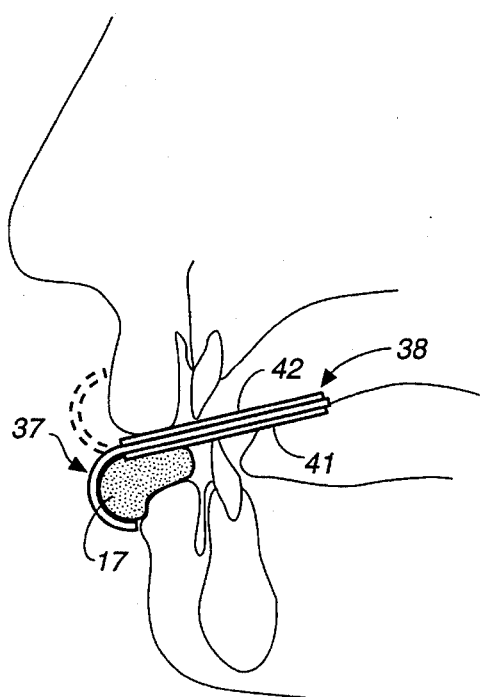
*FIG._7C*
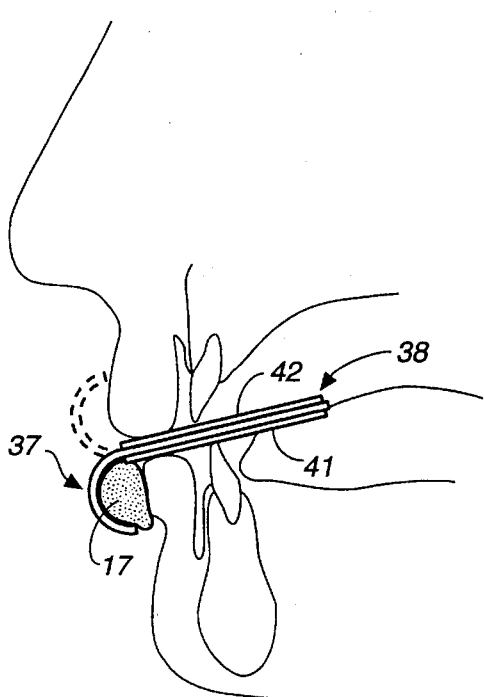
*FIG._7D*

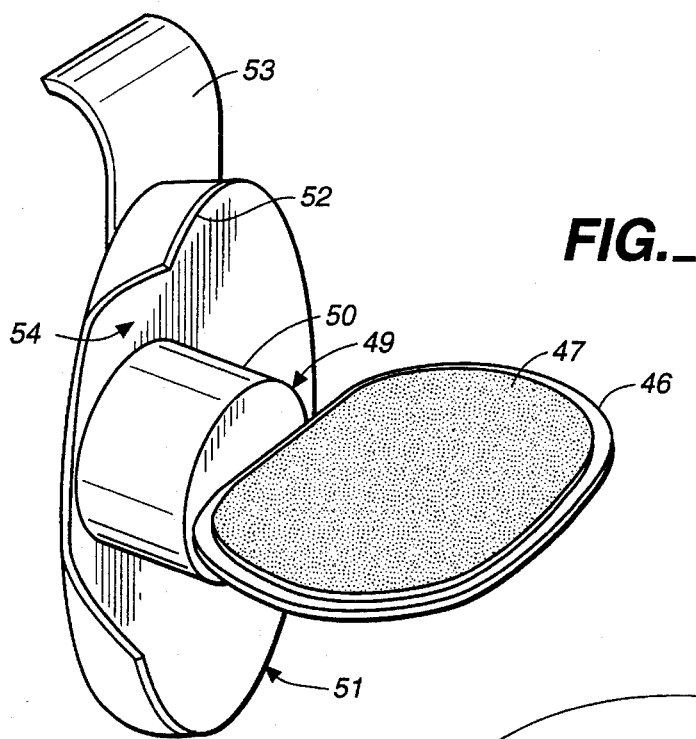
FIG._8
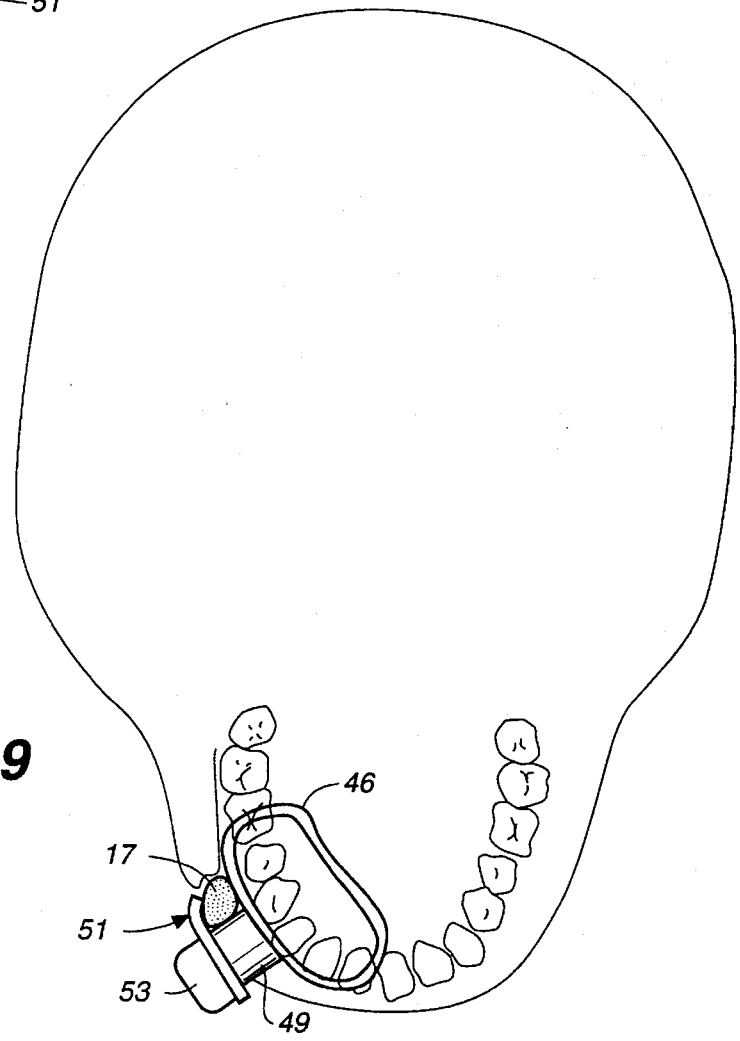
FIG._9

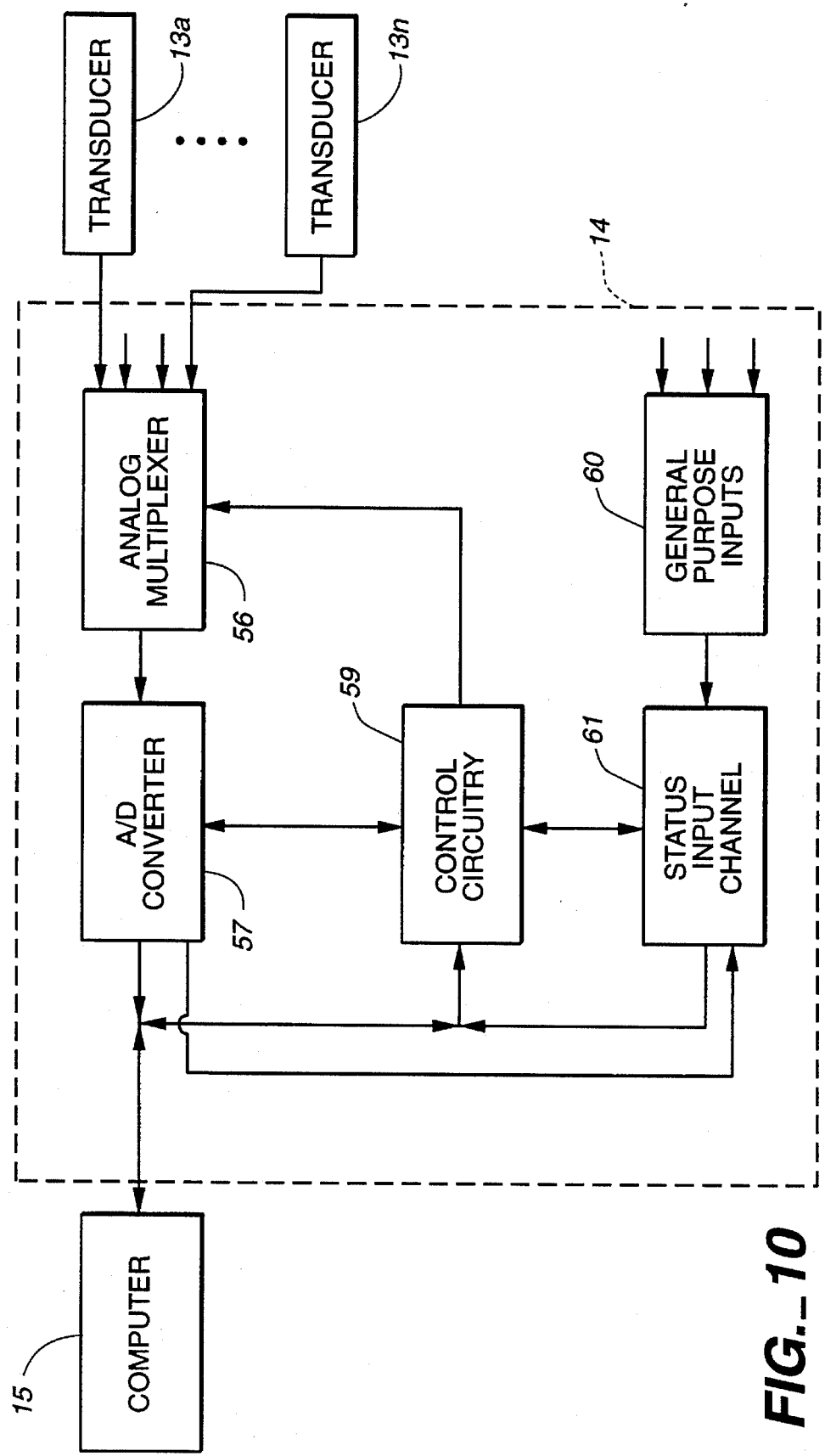
FIG._10

OROFACIAL MYOGRAPHIC MEASUREMENT METHOD

This is a division of application Ser. No. 08/184,294 filed Jan. 21, 1994, now U.S. Pat. No. 5,452,727.

BACKGROUND OF THE INVENTION

The invention relates generally to the field of myography and is more particularly directed to method for measuring characteristics of the lip and tongue muscles.

Myography is concerned with the measurement of contractions and relaxations of the skeletal muscles. In the diagnosis and treatment of various disorders involving the face and mouth, it is often desirable to determine the strength of the face and mouth muscles. Such determinations may be useful, for example, in assessing and treating certain speech disorders, in assessing the need for physical therapy for stroke victims, and for tracking progress in recovery from strokes or other injury to the mouth or face. Measurement of orofacial muscle strength may also be useful in connection with oral surgery, particularly where the musculature is to be cut. Measurements prior and post operation, for example, can aid in determining an appropriate course of isometric exercise or other physical therapy.

Although muscle strength measurements are recognized as a useful modality in diagnosis and assessment, in practice instrumentation for making direct measurements of orofacial muscle strength is not widely used. In one recent attempt to provide a directmeasurement orofacial instrument, for example, the patient "bites down" on a mechanical probe with the lips or pushes against the probe with the tongue and the instrument measures the strain induced in the probe with a strain gauge. From the strain gauge measurement the instrument gives a reading of the mechanical force of the patient's bite or push.

This type of instrument is subject to a number of drawbacks typical of the problems encountered with the direct measurement technique. It is difficult to obtain reproducibility of results because the measurement probes are sensitive to the precise positioning of the probe in the patient's mouth, that is, to the precise location at which the patient applies the force. In addition, a variety of different probe sizes are needed for different mouth sizes, and it then becomes more difficult to maintain a common calibration among the varied probe sizes.

In view of the uncertainty of direct strength measurements by known techniques, many practitioners either expect only rough, primarily subjective, estimates of muscle strength and consequently do not rely much on the strength-measurement modality, or they avoid direct force measurements altogether and instead use other techniques for monitoring muscle activity such as electromyographic measurements, which measure electrical response of the muscles.

SUMMARY OF THE INVENTION

The present invention provides a myographic measurement method for measuring the strength of the orofacial muscles, and in particular, the lip and tongue muscles, that provides greater reproducibility of measurement under conditions of and, is easy and efficient to perform, with apparatus that, and is economical to manufacture.

Briefly, a pressure-sensitive probe is placed in engagement with the orofacial muscle being tested. The probe provides a pressure response representative of the muscle strength under test. The probe is coupled to a transducer that converts the probe's pressure response in real time to an electrical signal representative of the force exerted on the probe by the muscle under test. The probe provides a representative pressure reading continuously over a test run of prescribed duration. The electrical signal generated in the test run is sampled and analyzed in real-time to determine a characteristic maximum pressure and hence characteristic maximum muscle strength achieved over the test run. The maximum muscle strength is provided in a form that may be incorporated directly into computerized patient records.

In the embodiment disclosed here the pressure-sensitive probe is provided by a balloon probe that is pneumatically coupled to a transducer. A strength measurement is made by holding the balloon probe against the muscle to be tested and having the patient press against the balloon probe with that muscle. To assist in holding the balloon probe in position a support fixture is provided that includes an anchor member that the patient retains in the mouth, typically gripped by the teeth, and a retaining member that is fixed to the anchor member and is shaped to retain the balloon probe in position against the lip muscle under test. Two illustrative shapes of support fixtures are discussed below for making measurements of the front upper and lower lip muscles and of lateral lip muscle the thrust.

Other aspects, advantages, and novel features of the invention are described below or will be readily apparent to those skilled in the art from the following specifications and drawings of illustrative embodiments.

BRIEF DESCRIPTION OF THE DRAWINGS

FIG. 1 is an overall perspective view showing a patient using apparatus according to the invention.

FIG. 2 is a block diagram showing an embodiment of apparatus for practicing to the invention.

FIG. 3 is a cross section of a balloon coupling.

FIG. 4 is an exploded perspective view of apparatus for forming the balloon coupling.

FIG. 5 is a schematic profile showing balloon probe positioning for tongue measurements.

FIG. 6 is a perspective view of a support fixture for use in measuring the strength of the front upper and lower lip muscles.

FIG. 7A is a schematic midline cross-section showing a balloon probe and support fixture of FIG. 6 in position for upper lip pressure directed downward toward the dental plane, and in phantom, the corresponding arrangement for the lower lip pressing upward.

FIG. 7B is a similar cross-section of an arrangement for pursing the lips for forward thrust as in making a u sound.

FIGS. 7C and 7D are similar to the cross section of FIG. 7A.

FIG. 8 is a perspective view of a support fixture for use in measuring the strength of lateral lip muscle thrust.

FIG. 9 is a schematic dental plane cross-section showing a balloon probe and support fixture of FIG. 8 where the lip pressure is directed toward the midline tangential to the dental arch with the probe wrapped around the pedestal of the support fixture.

FIG. 10 is a block diagram of electrical circuitry for operation with apparatus for practicing to the invention.

DETAILED DESCRIPTION OF ILLUSTRATIVE EMBODIMENTS

FIGS. 1 and 2 show an illustrative embodiment of a myographic measurement apparatus for practicing the invention. The apparatus includes a pressure-sensitive probe shown inserted in a patient's mouth and indicated generally by reference numeral 10. Probe 10 provides pressure readings relative to the ambient atmospheric pressure that are used for testing the strength of the desired muscle. In FIG. 1 the probe is shown inserted in the mouth of a patient 11 for making a measurement of the patient's tongue muscle strength. The probe is generally placed in engagement with the muscle to be tested in a manner to be described more fully below. When the patient exerts a force on the probe, the probe produces a pressure response representative of the strength of the muscle exerting the force. Probe 10 is connected to an instrument housing 12 that contains a transducer 13 for converting the pressure response from probe 10 into an electrical signal representative of the force exerted by the muscle. Housing 12 may include onboard front-end circuitry 14 for preamplifying or preliminarily conditioning the signal from transducer 13. Electronic circuitry (see FIG. 10), which may or may not be included within housing 12, receives the representative electrical signal from transducer 13 (or from the front-end circuitry 14) and converts it to a digital form to be received by a general purpose computer 15 for further processing. The circuitry may also provide the system power and receive commands from computer 15. As illustrated in FIGS. 1 and 2 the apparatus includes only a single probe 10. It may of course also be configured with a plurality of probes communicating with a respective plurality of transducers contained in a single instrument housing. In this configuration the circuitry will also include switching circuitry for selecting amongst the plurality of probes.

Probe 10 is held against the muscle under test, and the muscle exerts a force against the probe. In the past, direct force measurements such as this have been lacking in their precision and reproducibility of results. The problem arises in trying to isolate the force exerted by a particular muscle in a particular direction without introducing uncertainties and unreproducible factors associated with mechanical linkages or other mechanical aspects of the apparatus. According to the present invention probe 10 is a pressure-sensitive probe that may be conveniently applied directly to the muscle under test at a variety of positions to measure muscle strength in different directions and is responsive to the pressure rather than to the total force that the muscle exerts. As illustrated in FIG. 2 probe 10 may be provided by a balloon 17 that is removably connected through coupling 19 of FIG. 3 and air line 18 to instrument housing 12. All pressure line connections are easily made by hand using standard techniques that give tight seals. A squeeze bulb 21 is provided for pumping up balloon 17 with an initial charge of air. Squeeze bulb 21 is connected to instrument housing 12 by air line 22, which is connected within the housing through a lever-action inlet valve 23 and junction 24 to air line 18 and balloon 17. Bleed valve 25 is provided for bleeding the air from balloon 17. The structure and operation of squeeze bulbs is familiar, for example, from their use in connection with sphygmomanometers for measuring blood pressure and thus need not be disclosed in detail here. Transducer 13 is connected to air line 18 through junction 24 for communicating pressure variations from the air line to the transducer.

For accurate measurement it is important that the coupling of balloon 17 to air line 18 not leak during a test sequence. A suitably hermetic seal may be achieved with the following construction of coupling 19 described with reference to FIG. 3. A solid plug 26 is disposed in the neck of balloon 17. Plug 26 has a central aperture, into which a brass tube 27 is press-fit for attachment in standard fashion to air line 18. A collar 28 of heat-shrinkable plastic is placed around the neck of the balloon and plug 26 and heat is applied to the collar causing it to shrink down around the neck and hold the balloon securely to plug 26. The outer surface of plug 26 may be formed with grooves such as illustrated at 29 in FIG. 3 for receiving the deformed skin of balloon 17 and providing an airtight seal.

To be assured of an airtight seal, it is desirable to apply heat to collar 28 uniformly around its circumference. Uniform heating is achieved with the apparatus of FIG. 4, which comprises a rotatable support member 31 for supporting plug 26 and a heating coil 32 for applying heat to heat-shrinkable collar 28. Support member 31 includes a base portion 33 for coupling to a motor (not shown) and a shaft 34 for receiving and frictionally engaging brass tube 27. The heating coil is formed with a coil diameter permitting the coil to loosely surround the neck of a balloon assembled with plug and heat-shrinkable collar in position. In operation, a balloon neck is placed over plug 26 and surrounded with an unshrunk collar 28. The assembly is mounted on shaft 34 and positioned so heating coil 32 surrounds collar 28. Support member 31 together with the collar assembly mounted thereon are rotated slowly (e.g., on the order of 60 revolutions per minute) around a generally horizontal axis as an electrical current is applied to coil 32. With this arrangement the coil heats collar 28 uniformly, which then shrinks down with uniform tightness around the neck of the balloon. Because of the tendency of heated air to rise, it has been found that more uniform heating, and hence more uniform tightness, has been achieved when shaft 34 and collar 28 are rotated about an approximately horizontal axis as opposed to a vertical or substantially inclined axis.

The use of a balloon probe is desirable for a number of reasons. Balloons are inexpensive so that it is cost effective merely to discard a balloon after use by a patient. This avoids the need for sterilizing the probe after each use and thus saves time and the considerable cost of sterilization equipment. Operating on pneumatic principles, the balloon probe is responsive to very small changes in pressure, may readily be deformed to fit into engagement with the muscles of the lips and mouth in various configurations, and the resulting measurement is independent of the area of contact between the muscle and the balloon and the direction in which the muscle force is exerted. While the use of a hydraulic probe will also provide a number of these qualities, a pneumatic probe is preferred because the measurement will be independent of any hydrostatic head associated with the relative height with which a hydraulic probe is used and thus there is no need for special circuity or calibration to correct for the hydrostatic head. In a pneumatic probe care must be taken to account for the compressibility of air or other gas. Boyle's Law for gases at constant temperature states that for a given quantity of gas the pressure and volume vary inversely. For example, the internal volume of the rest of the system cannot exceed the starting volume of the balloon if the absolute pressure is to be doubled when the balloon is pressed flat. If a greater range of pressure change is desired, the compressible volume of air may be reduced by replacing the air in the working volume of the transducer and part of the tubing in the instrument housing with a non-toxic hydrocarbon compound of low volatility such as mineral oil. No error from differential hydrostatic head will be observed if all tests are performed with the instrument housing level.

Although a disposable balloon 17 is desirable for the reasons just described, those skilled in the art will recognize that a pressure-sensitive pneumatic probe meeting the purposes of the invention may be formed in other ways. For example, a stretchable balloon-like membrane may be mounted in a probe housing to form a wall of a reservoir chamber for air or other gas. The probe housing may be shaped so that the membrane presents a convenient surface for engagement with the patient's lip or tongue.

FIG. 5 illustrates the positioning of a balloon probe 17 for making measurements of the strength of a patient's tongue muscles. The probe is inserted into the patient's mouth typically against the anterior position of the hard palate just behind the alveolar ridge. Alternatively, the balloon may be placed in a posterior position against the anterior incisors with the tongue pressed up against the anterior incisors. On command the patient presses against the balloon with the anterior and medial positions of the tongue 36 which are the areas having the most thrust. The force of the tongue against the balloon is translated into an increase in the pneumatic pressure of the air in air line 18, which is communicated to transducer 13. The transducer converts this pressure increase into an electrical signal for further processing. The representative electrical signal thus generated is independent of the particular location at which the tongue contacts the probe and does not require any correction for mechanical distortions caused by some probes such as leverage or other mechanical advantage artificially enhancing or diminishing the applied force.

In making strength measurements of the upper and lower labial regions, the balloon probe is used in conjunction with an ancillary supporting fixture such as illustrated in FIG. 6. The support fixture of FIG. 6 includes a retaining member indicated generally at reference numeral 37 which is formed to retain the balloon in position against the pressure exerted by the lip muscle being tested. The support fixture of FIG. 6 also includes an anchor member indicated generally at reference numeral 38 which is formed and sized to be retained conveniently in the mouth for anchoring the fixture during the measurement. For the upper and lower labial strength measurement retaining member 37 is provided by a curvate or angular end portion 39 which defines a generally elongate concavity or recess 40 for receiving balloon 17. As illustrated in FIG. 6 anchor member 38 is generally planar and has a width comparable to the separation of the left and right rows of teeth. The support fixture also includes replaceable protective pads 41 and 42 on the upper and lower surfaces of anchor plate 42. Pads 41 and 42 provide a cushion for gripping by the teeth and are preferably removable for cleaning and/or replacement. Pads 41 and 42 may be provided, for example, by a planar rubberized magnetic pad generally conforming to the shape of anchor member 42. When the pads 41 and 42 are formed of a magnetic material, the support member must of course also be formed of a magnetically active material such as Type 430 stainless steel. The pads are magnetized merely to hold them in position on anchor plate 38.

Measurements of upper and lower labial strength are described with reference to FIGS. 7A and 7B. For the upper labial measurement balloon probe 17 is inflated and positioned in concavity 40. Anchor member 38 is inserted in the patient's mouth so that pad 42 on the underside rests against the lower teeth. For the measurement shown in either FIG. 7A or 7B, the patient's upper lip engages and presses against balloon 17, which is held securely in position by retaining member 37. For the measurement shown in FIG. 7A the patient's upper lip engages balloon 17 at its upper surface and exerts a downward force. For the measurement shown in FIG. 7B the patient's upper lip engages balloon 17 at its posterior surface and exerts a forward force such as in forming a long "u" sound. For either of the measurements the increase in pneumatic pressure within the balloon is communicated to transducer 13. To measure the lower labial strength, the fixture is inserted in the patient's mouth upside down, i.e., with the concavity formed by inverted retaining member 37' on the underside of the fixture as shown in phantom in FIGS. 7A and 7B. The patient applies pressure with the lower lip to balloon 17'. The measurement then proceeds as with the upper labial measurement.

For lateral strength measurements an appropriate ancillary support fixture is illustrated in FIG. 8. The support fixture includes an anchor plate 46 which is inserted in the patient's mouth and which has a horizontal extent sufficient to be gripped and held securely by the teeth along one side of the mouth. As in the fixture for the upper and lower labial strength measurements, anchor plate 46 is also provided with protective pads 47 on the upper and lower surfaces of the anchor plate. This support fixture also includes a retaining member indicated generally at reference numeral 48 formed to retain the balloon in position at the corner of the patient's mouth against lateral pressure of the lip muscle being tested. In the embodiment of FIG. 8 retaining member 48 comprises a pedestal 49 fixed to an edge of anchor plate 46 providing a surface indicated at 50 for resisting movement of the balloon and a member 51 mounted on pedestal 49 also for resisting movement of the balloon. Member 51 is formed with a cup-shaped portion 52 for retaining the balloon in position. As illustrated in FIG. 8 member 51 has a handle portion 53 by which the patient or practitioner may conveniently grasp the fixture to adjust its position when in the patient's mouth. To make grasping easier, handle portion 53 may be bent away from anchor plate 46. A curved edge of cup-shaped portion 52 may be partially cut away as indicated at reference numeral 54 to provide an exit passageway for an air line attached to a probe nestled in cup-shaped portion 52.

In use, anchor plate 46 is inserted in the patient's mouth to one side or the other and is held in that position by the patient's teeth against protective pads 47. Pedestal surface 50 and cup-shaped portion 52 of member 51 together with the patient's face at the corner of the mouth form a concavity for receiving the balloon. Arranged in this way, the fixture helps maintain the balloon in vertical disposition at the corner of the mouth so that some portion of the balloon is in contact with the lower lip at the corner of the mouth. This is a desirable goal because the lower lip is generally the weak portion responsible for droop and thus is typically an area one desires to evaluate. FIG. 9 shows a diagrammatic view of the top of a patient's head with a balloon 17 mounted in the lateral measurement fixture against the side of the patient's mouth. With the fixture and balloon mounted in this configuration, the force is applied to the balloon by the corner of the lip.

Electric circuitry for use with the invention is now described with reference to FIG. 10. The circuitry may be mounted for example on an input/output board installed in general-purpose computer 15. FIG. 10 illustrates a plurality of transducers 13a, . . . , 13n for supporting a plurality of probes in one instrument. The pressure response of an individual probe 10 is applied to one of the transducers, say, transducer 13a, through an appropriate junction or other mixing device. Transducer 13a converts the pressure response of the probe into an electrical signal representative of the muscle activity. Appropriate transducers are well known and commercially available. They need not be described in further detail here.

Multiplexer 56 selects the transducer connected to the active probe. The raw electrical signal from the selected transducer is applied to an analog-to-digital converter 57 (ADC), which provides the raw signal in digital form along line 58 to computer 15. These components are standard and need not be described in detail here. Control circuitry 59 is conventional circuitry for controlling communications with the computer and for responding to computer commands to control the ADC, multiplexer, and any other diagnostic or supplementary circuitry. General purpose inputs 60 and status input channel circuitry 61 are provided for diagnostic and maintenance purposes. These may be provided by conventional circuitry and do not constitute a part of the present invention.

In the specific embodiment disclosed here computer 15 includes software routines for controlling the ADC subsystem and for implementing data collection from the test probes. Computer 15 will also generally include other software routines for maintenance and patient data processing tasks not forming a part of the present invention. A listing of a specific software routine implementing the data collection aspects of the present invention is given at the end of this specification. The routine is written in the C language and will be readily comprehensible to those skilled in the art of C programming given the descriptions provided herein and the mnemonics and comments included in the listing. The listing is labeled by the C language label PDC.C standing for patient data collection.

The raw representative signal applied to A/D converter 57, and hence the signal presented to the computer along line 58, is provided continuously, as long as a test continues. The signal will generally rise and fall as the patient voluntarily or reflexively exerts more or less thrust against the probe and will reach a maximum at the point of maximum muscle thrust. The computer repeatedly samples the test signal from ADC 57 at 30-millisecond intervals and takes the maximum sampled value as representative of the maximum strength measurement, which the instrument then records as the test result. PDC.C is made up of the following principal subroutines, which have the following functions. CaptureData is the subroutine that collects a run of data from a test run and returns the largest value found. ParseParms checks for command line parameters. GetChar gets characters from the computer keyboard. ADCerror displays any ADC error. DisplayHelp displays a help screen if an unintelligible command line is found. In operation, PDC.C displays a menu of tests to the operator who selects the desired test. PDC then runs the selected test.

To begin the sampling process, CaptureData is fed the keystroke character (e.g., 0–9 or A–Z) designating the selected test. CaptureData then calls upon ADC driver routines to read the ADC. The ADC driver includes subroutines for the following functions: SetupADC sets up the ADC subsystem. SetADCChannel selects the desired channel from which the ADC reading is to be acquired. ADCbusy determines whether the ADC input channel is busy. If the input channel is busy, the computer assumes that the ADC is in the process of converting data and is thus not ready. ReadADC takes a single reading from the ADC subsystem. More specifically, CaptureData repeatedly calls ReadADC, which in turn calls SetADCChannel, which sets the desired channel from multiplexer 56. When the channel is set, ReadADC initiates the ADC. ReadADC then repeatedly calls ADCbusy to determine if the ADC is ready, that is, whether it has finished converting test data. When the ADC is ready, PDC then saves a first reading, waits 30 milliseconds, takes a second reading, saves it, and continues in this manner until it has taken 300 readings or until a keystroke Q ends the test, whichever occurs first. At this point the read phase is terminated. After each reading session PDC selects the largest value and saves it internally until it is decided to keep it as a final test value. In the code listing illustrated here the final readings are stored with patient data by means of the routine SavePData. The remaining readings are saved in <test><date>.tst for possible future use.

RTC_DVR is the real-time clock driver, and TMR_DVR is a timer driver. TMR_DVR provides a clock tick every millisecond, which allows the test to be run with one-millisecond accuracy. The other functions and subroutines of the listing will be readily understood by those skilled in the art insofar as they pertain to the above descriptions.

The above descriptions and drawings disclose illustrative embodiments of the invention. Given the benefit of this disclosure, those skilled in the art will appreciate that various modifications, alternate constructions, and equivalents may also be employed to achieve the advantages of the invention. For example, although pressure-sensitive probe 10 has been illustrated here as a pneumatic probe in the form of a balloon, those skilled in the art will recognize that other forms of pressure-sensitive probes now known or later developed may be substituted for the pneumatic probe to serve the same functional and operational purpose. Therefore, the invention is not to be limited to the above description and illustrations, but is defined by the appended claims.

OROFACIAL MYOGRAPHIC MEASUREMENT APPARATUS

PDC.C

```c
#include "stdio.h"
#include "conio.h"
#include "io.h"
#include "dos.h"
#include "int.h"
#include "gt_tools.h"

#define FALSE 0
define TRUE !FALSE                    /* Logical Truths */ define _DATE_ "940110"
define _VER_  "1.3 "

#define LF  0x0a
#define CR  0x0d
define ESC 0x1b include "adc_dvr.h"
include "rtc_dvr.h"
#include "tmr_dvr.h"
#include "pdata.h"

int _stack = 16384;

int debugmode = FALSE;
int testmode  = FALSE;
int baseaddr  = DEFAULT_BASE_ADDR;

char setup_file[64] = INIT_FILE;
unsigned char RTCbuffer[64];
char Today[ DATE_STRING_LEN ];

int ADCbuffer[300];
int page;
int risingThresh  = 0;
int fallingThresh = 0;

void ADCerror( void );
int  CaptureData( int TestNum );
void DisplayHelp( void );
int  GetChar( void );
void ParseParms( int i, char *parms[] );

int main( int argc, char *argv[] )
{
    int i, j, k;
    int MaxADCval, PrevADCval, ADCval;
    FILE *fp;
    struct INT_DATA pd;
    int TestCode;
    int retval;
    double Val;

PrevADCval = MaxADCval = 0;
    retval = FALSE;

if ( debugmode )
        printf( "\n   Getting date" );
    ReadRTC( RTCbuffer );
    sprintf( Today, "%02x%02x%02x", RTCbuffer[8], RTCbuffer[7] );
    RTCbuffer[9], RTCbuffer[8], RTCbuffer[7] );

ParseParms( argc, argv );
    page = GetPage();

outp( 0x43, 0x34 );                 /* Make sure of timer setup */
    outp( 0x40, 0xa9 );                 /* Set timer to 1.0 ms      */
    outp( 0x40, 0x04 );                 /*                          */
    Int_Intercept( 0x08, TimerIntercept, 256 );

SetupADC();
    InitPData();
    LoadPData( TRUE );

do {
        if ( !debugmode ) {
            cls( F_WHITE );
            GotoXY( 10, 1, page );
            printf( "Patient Data Collection   V%s %s", _VER_, _DATE_ );
            GotoXY( 20, 3, page );
            printf( "Patient : %s", PName );
            GotoXY( 20, 4, page );
            printf( "Date    : %s", Today );
            for ( j=k=0; j<NUMTESTS; j++ ) {
                if ( *pData[j].TestName ) {
                    GotoXY( 4, 10+ (k++), page );
                    printf( " %c - %s ", TestSet[j], pData[j].TestName );
                }
            }
        }
        if ( !retval ) {
            GotoXY( 5, 6, page );
            printf( "Result of %s  test is : %.2f %s",
                    pData[j].TestName, Val, pData[j].Unit );
        }
        GotoXY( 5, 8, page );
        printf( " Enter desired test code (or press 'Esc' to quit) : " );
        TestCode = GetChar();
```

PDC.C  1-10-94  2:14a                                                  Page 1

```c
        if ( !debugmode ) {
            else F_WHITE );
            GotoXY( 10, 1, page );
            printf( "Patient Data Collection v%s %s", _VER_, _DATE_ );
            GotoXY( 20, 3, page );
            printf( "Patient : %s", PName );
            GotoXY( 5, 5, page );
        }

TestCode = toupper( TestCode );
        for (i=0;i<NUMTESTS;i++) {
            if ( TestSet[i] == TestCode ) {
                break;
            }
        }
        if ( i >= 0 ) {
            retval = CaptureData( i );
        } if ( ( retval >=0 ) && ( retval <16384 ) ) {
            val = (retval-pData[i].Offset) *pData[i].Scale;
            retval = TRUE;
        } else {
            retval = FALSE;
        }
    } while ( TestCode != ESC );

SavePData();

outp( 0x43, 0x34 );              /* Make sure of timer setup   */
    outp( 0x40, 0xff );              /* Put timer back to 18.2 Hz  */
    outp( 0x40, 0xff );              /*                            */ i = _int_restore( 0x08 );
    if ( debugmode )
        printf( "\n  Ints restored; return value = %x", i );

printf( "\n\n\nProgram done\n\n" );

return (0);
}

/* Do a test; return largest value found */ int CaptureData( int TestNum )
{
    int i, j, k;
    FILE *fp;
    int MaxADCval, PrevADCval, ADCval;
    char OutFileName[64];
    char buff[10];
    int Testing;

if ( !debugmode ) {
        GotoXY( 10, 6, page );
        printf( "Performing %s test :", pData[TestNum].TestName );
        GotoXY( 10, 8, page );
        printf( "Press 'q' to stop, or 'Esc' to abort" );
    } if ( debugmode )
        printf( "\n Starting" );
    for ( i=0; i<10; i++ ) {
        for ( j=0; j<30; j++ ) { if ( Testing && bioskey(1) ) {
                switch ( tolower(GetChar()) ) {
                    case ESC:                    /* Abort the test: */
                        return ( 32767 );        /* Stop the test:  */
                    case 'q':
                        Testing = FALSE;
                        break;
                }
            } if ( !Testing ) {                    /* Test stopped? If so, clear data */
                ADCbuffer[ (i*30) +j ] = 0;
                continue;
            }

ADCbuffer[ (i*30) +j ] = ADCval = ReadADC( 0 );

if ( ADCval<0 ) {                    /* Any problems reading the ADC? */
                ADCerror();                      /* Yes - Tell the operator...    */
                return ( 32767 );                /*        ...and quit            */
            } if ( !debugmode ) {
                if ( ADCval<0 ) ADCval = 0;
                if ( ADCval>4095 ) ADCval = 0;

GotoXY( j+20, i+11, page );
                WriteChar( '*', B_BLACK | F_WHITE, page );

if ( MaxADCval < ADCval ) {
                    k = MaxADCval>>6;
                    for ( ; k<(ADCval>>6); k++ ) {
                        GotoXY( k+15, 23, page );
                        WriteChar( '*', B_BLACK | F_WHITE, page );
                    }
                    MaxADCval = ADCval;
                } k = PrevADCval>>6;
                GotoXY( k+15, 24, page );
                WriteChar( ' ', B_BLACK | F_WHITE, page );
                k = ADCval>>6;
                GotoXY( k+15, 24, page );
                WriteChar( '*', B_BLACK | F_WHITE, page );
                PrevADCval = ADCval;
            } else {
                if ( MaxADCval < ADCval )
                    MaxADCval = ADCval;
            }
        }
    } strcpy( OutFileName, Today );
    if ( pData[TestNum].Num < pData[TestNum].New )
        pData[TestNum].Num++;
    pData[TestNum].Capture[MAXCAPS].val = MaxADCval;
    strcpy( pData[TestNum].Capture[MAXCAPS].date, OutFileName );

if ( debugmode )
        printf( "\n        Got date; Generating file name" );
    sprintf( OutFileName, "%c-%s.DAT", CapSet[TestNum], Today );

if ( debugmode )
        printf( "\n        File name is \"%s\"", OutFileName );
```

```c
    fp = fopen( OutFileName, "wb" );
    if ( fp ) {
            printf( "\n    File opened" );
        else
            printf( "\n    Error opening file" );
    if ( fp ) {
        fwrite( ADCbuffer, sizeof(int), 300, fp );
        fclose( fp );
        if ( debugmode )
            printf( "\n    Data written, file closed" );
    }
    if ( strcmp( PDLV, Today ) || !atoi( PTNV ) ) {
        strcpy( PDLV, Today );
        sprintf( PTNV, "%d", atoi( PTNV ) +1 );
    }
    return ( MaxADCval );
} void ParseParms( int i, char *parms[] )
{
    char *parm;
    int tempThresh;

while ( --i ) {
        parm = *(++parms);
        if ( *parm != '-' && *parm != '/' ) continue;
        switch( tolower( parm[1] ) ) {
            case 'd':
                debugmode = TRUE;
                break;
            case 'f':
                strcpy( setup_file, parm+2 );
                break;
            case 't':
                switch ( tolower( parm[2] ) ) {
                    case '\0':
                        testmode = TRUE;
                        break;
                    case 'f':
                    case 'r':
                        sscanf( parm+3, "%d", &tempThresh);
                        if ( tolower( parm[2] ) == 'r' )
                            risingThresh = tempThresh;
                        else
                            fallingThresh = tempThresh;
                        break;
                }
                break;
            case 'h':
            case '?':
                DisplayHelp();
                exit();
                break;
        }
    }
}

/******************************************************************
*
*   GetChar()
*
*       Gets characters from the keyboard
*
*       If regular key struck, returns ASCII code
*       If special key struck, returns 0x100 ORed to KBD scan code
*
******************************************************************/
int GetChar( void )
{
    int InChar;

InChar = getch();
    if ( InChar==0x00 || InChar==0xe0 )
        InChar = 0x0100 | getch();
    return ( InChar );
}

/******************************************************************
*
*   ADCerror()
*
*       Something's wrong with the ADC
*
*       Display an error message and wait for the user to respond
*               before continuing on our merry way....
*
******************************************************************/
void ADCerror( void )
{
    fputs( "\n\n\n\n         \007Error accessing ADC\n", stderr );
    fputs( "                 \n         Press any key to continue :", stderr );
    GetChar();
} void DisplayHelp()
{
    fputs( "\n             Program Options :\n", stderr );
    fputs( "\n   -d        Switch debug mode on", stderr );
    fputs( "\n   -f        Change standard setup file", stderr );
    fputs( "\n   -t        Switch to test mode", stderr );
    fputs( "\n   -tf       set the threshold (falling data values)", stderr );
    fputs( "\n   -tr       set the threshold (rising data values)", stderr );
    fputs( "\n   -?        Display this help message", stderr );
}
```

What is claimed is:

1. A method of measuring the strength of an orofacial muscle of a patient comprising the steps of:

applying a pressure-sensitive probe to engage aid orofacial muscle, said probe being yieldable in response to contraction of said orofacial muscle;

contracting said muscle to exert pressure on said probe;

sensing the pressure exerted on said probe by said orofacial muscle;

providing an electrical signal in real time representative of the pressure exerted on said probe by said orofacial muscle over the duration of a test run;

deriving from said electrical signal a characteristic maximum value thereof over the duration of said test run, wherein said maximum value of said electrical signal is characteristic of the maximum pressure exerted by said orofacial muscle over the duration of said test run; and recording a maximum muscle strength value corresponding to said characteristic maximum value of said electrical signal over the duration of said test run.

2. The method of claim 1 wherein said step of applying a pressure-sensitive probe comprises the step of inserting a pressure-sensitive probe in the patient's mouth and said step of contracting said muscle to exert pressure on said probe comprises the step of pressing against said probe with the patient's tongue.

3. The method of claim 2 wherein said step of inserting a pressure-sensitive probe in the patient's mouth comprises the step of inserting a pneumatic balloon probe into the patient's mouth.

4. A method of measuring the strength of an orofacial muscle of a patient comprising the steps of:

inserting a support fixture into the patient's mouth, said support fixture having an anchor portion to be grasped by the patient's teeth and a retaining portion protruding from the patient's mouth for receiving said probe;

applying a pressure-sensitive probe to engage a lip muscle of the patient by inserting said probe between said retaining portion and a region of said lip muscle;

contracting said muscle to exert pressure on said probe by pressing against said probe with said region of said lip muscle;

sensing the pressure exerted on said probe by said region of said lip muscle;

providing an electrical signal in real time representative of the pressure exerted on said probe by said region of said lip muscle over the duration of a test run;

deriving from said electrical signal a characteristic maximum value thereof over the duration of said test run, wherein said maximum value of said electrical signal is characteristic of the maximum pressure exerted by said region of said lip muscle over the duration of said test run; and recording a maximum muscle strength value corresponding to said characteristic maximum value of said electrical signal over the duration of said test run.

5. The method of claim 4 wherein said step of inserting said probe comprises the step of inserting a pneumatic balloon probe between said retaining portion and said lip muscle region.

* * * * *